United States Patent [19]
White et al.

[11] Patent Number: 6,045,557
[45] Date of Patent: Apr. 4, 2000

[54] DELIVERY CATHETER AND METHOD FOR POSITIONING AN INTRALUMINAL GRAFT

[75] Inventors: Geoffrey H. White, East Balmain; Weiyun Yu, Five Dock, both of Australia

[73] Assignee: Baxter International Inc., Deerfield, Ill.

[21] Appl. No.: 09/068,589

[22] PCT Filed: Nov. 10, 1996

[86] PCT No.: PCT/AU96/00714

§ 371 Date: Aug. 17, 1998

§ 102(e) Date: Aug. 17, 1998

[87] PCT Pub. No.: WO97/17911

PCT Pub. Date: May 22, 1997

[30] Foreign Application Priority Data

Nov. 10, 1995 [AU] Australia ................... PN6512
Nov. 10, 1995 [AU] Australia ................... PN6513
Nov. 10, 1995 [AU] Australia ................... PN6514

[51] Int. Cl.$^7$ ........................................ A61F 2/06
[52] U.S. Cl. ........................................... 606/108
[58] Field of Search .................... 606/108, 191, 606/192, 194, 195; 623/1

[56] References Cited

U.S. PATENT DOCUMENTS 4,994,071  2/1991  MacGregor ..................... 606/194
5,562,726  10/1996  Chuter .............................. 606/195
5,609,627  3/1997  Goicoechea et al. ........... 606/108
5,628,783  5/1997  Quiachon et al. ................ 606/195

FOREIGN PATENT DOCUMENTS 0508473  10/1992  European Pat. Off. ........... 606/108
9508966  4/1995  WIPO ................................ 623/1
9513033  5/1995  WIPO ................................ 623/1

*Primary Examiner*—Jeffrey A. Smith
*Assistant Examiner*—Eduardo C. Robert
*Attorney, Agent, or Firm*—Baxter Healthcare Corp.; Bruce M. Canter; Peter Jon Gluck

[57] ABSTRACT

A delivery catheter and method for positioning an intraluminal graft within a branching vessel in a patient's body and a delivery catheter for use in that method is described. The delivery catheter comprises an elongate catheter having preferably an inflatable balloon adjacent one end, an intraluminal graft disposed about the balloon that bifurcates into two short tubular extensions, and a thin supplementary catheter containing a guidewire that extends upstream through one of the first tubular extensions and downstream through the other of the short tubular extensions of the graft. The method for positioning the intraluminal graft using the delivery catheter is particularly applicable to the appropriate positioning of a trouser graft so that it bridges an aneurysm which extends from a single vessel, such as the aorta, into one or more divergent vessels, for example, an iliac artery.

48 Claims, 14 Drawing Sheets

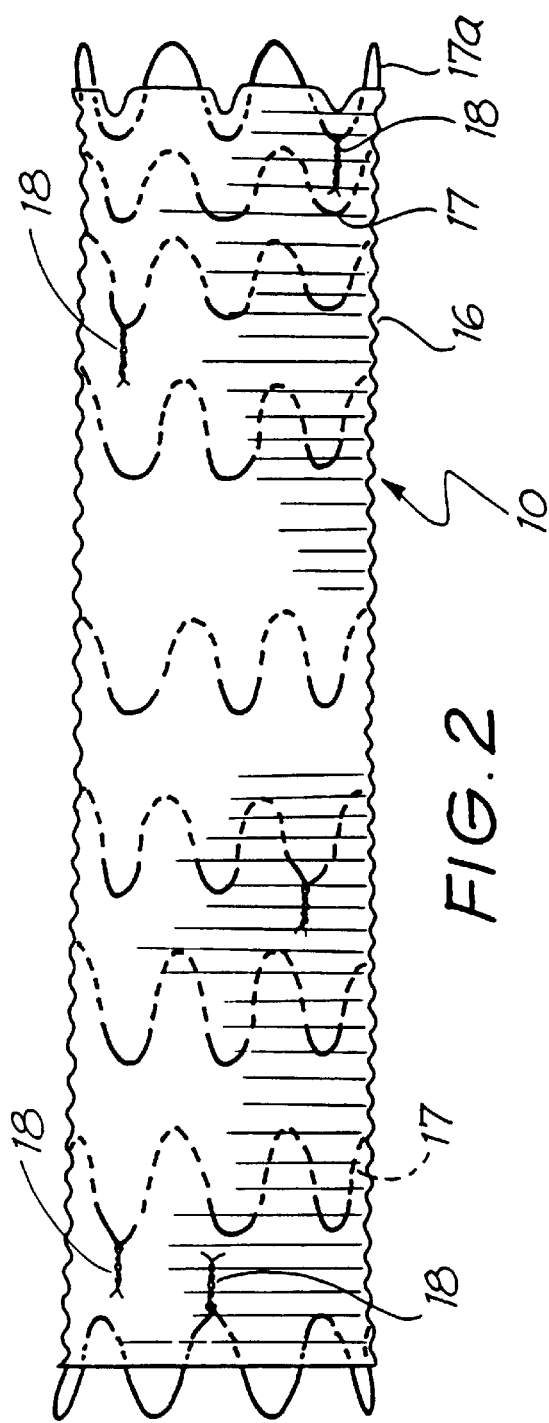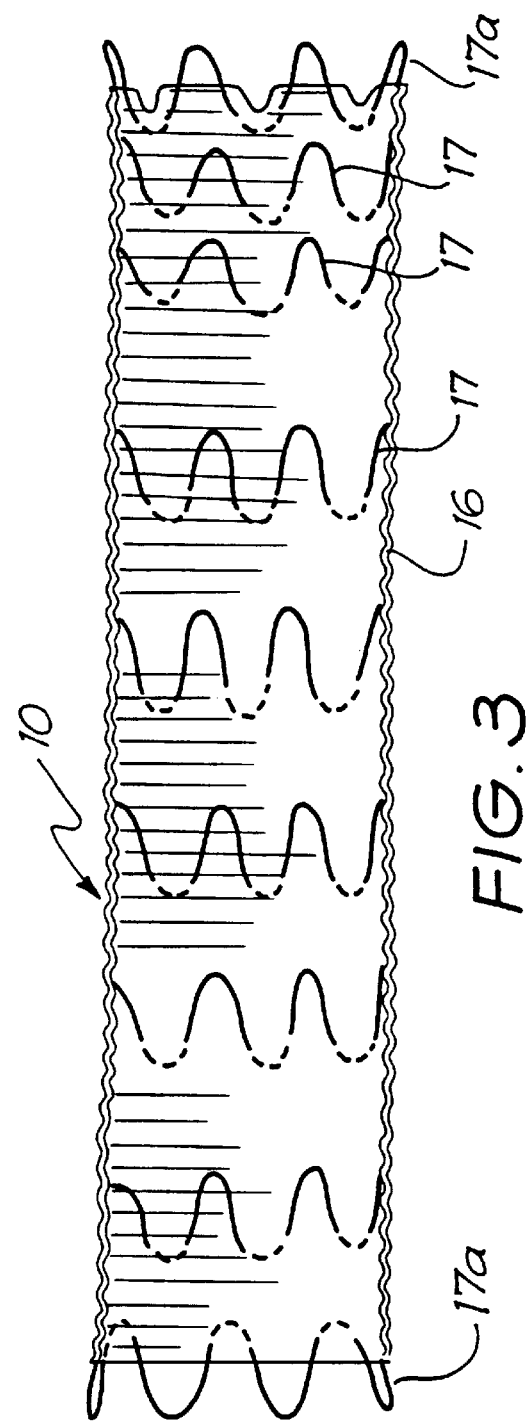

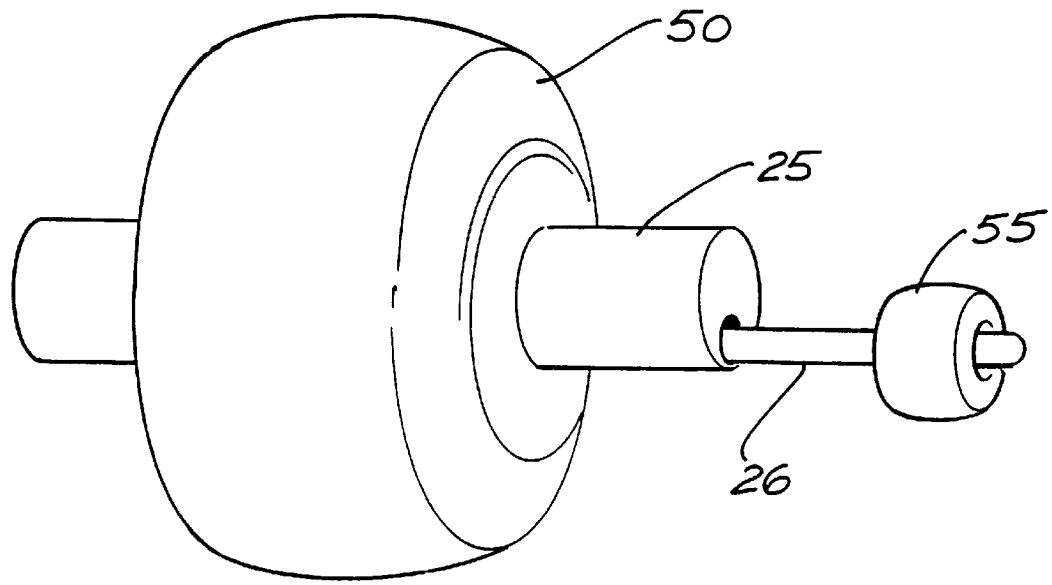
FIG. 6b
FIG. 6c
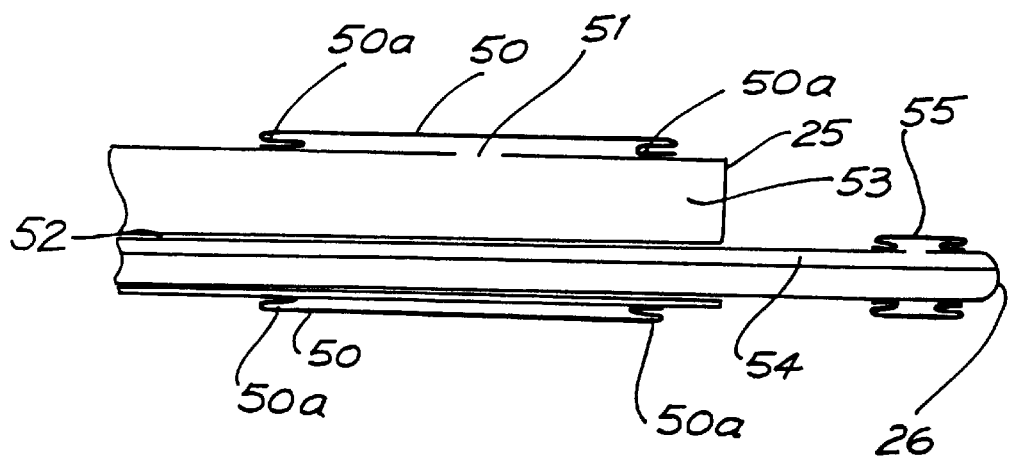

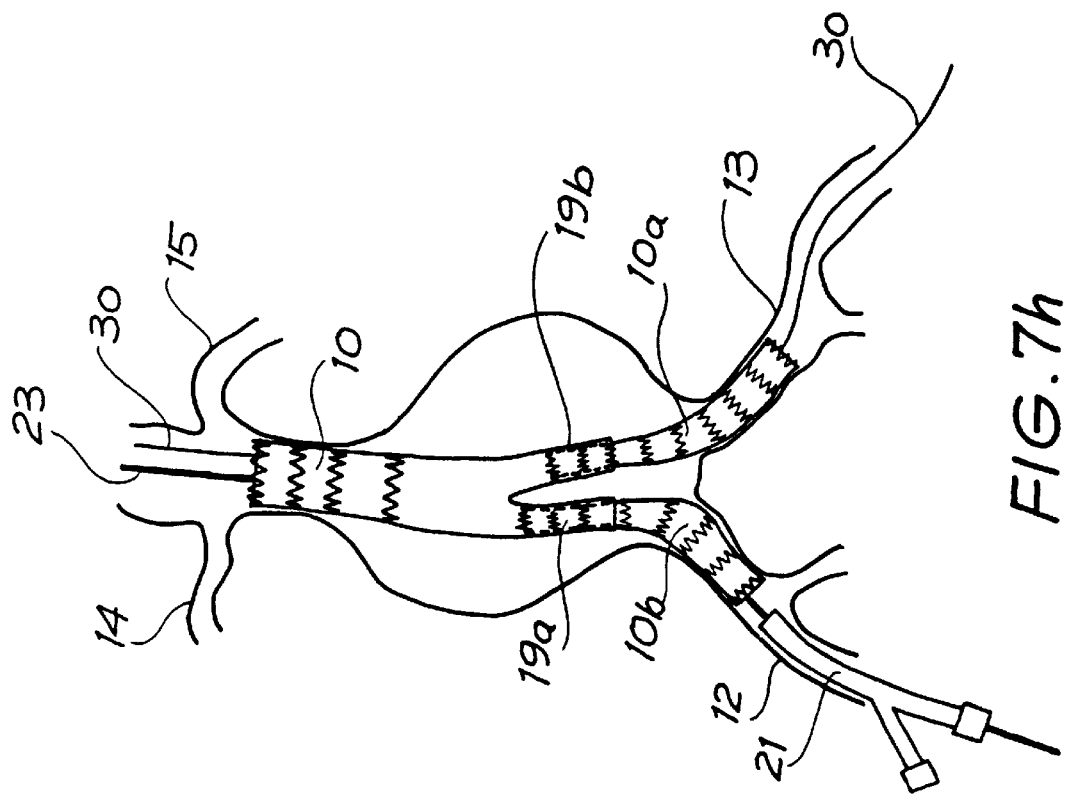
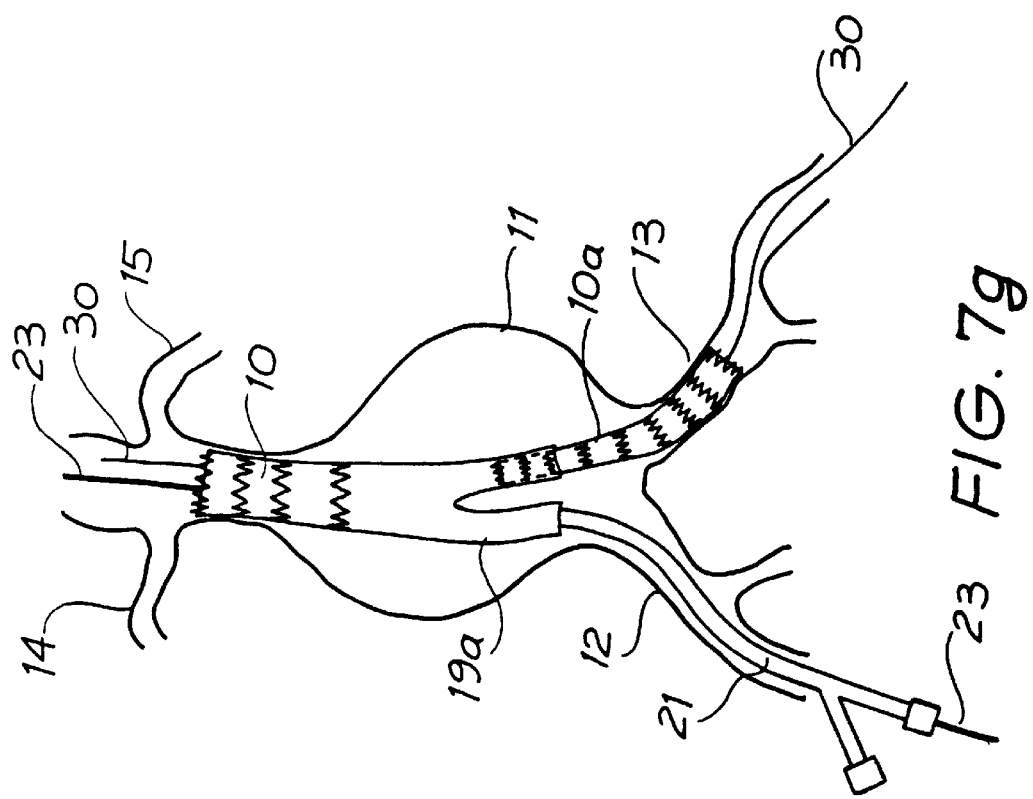
FIG. 7h
FIG. 7g

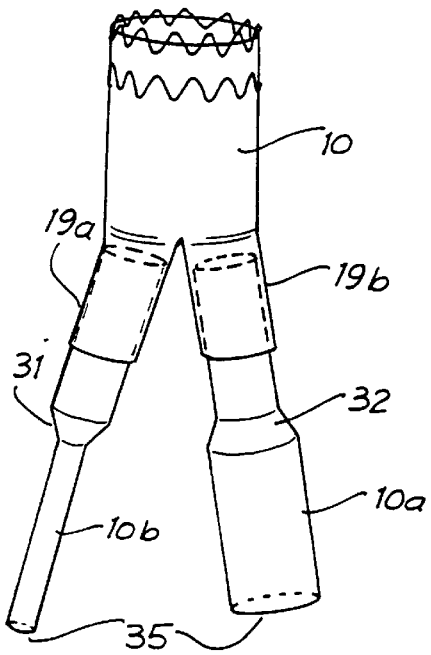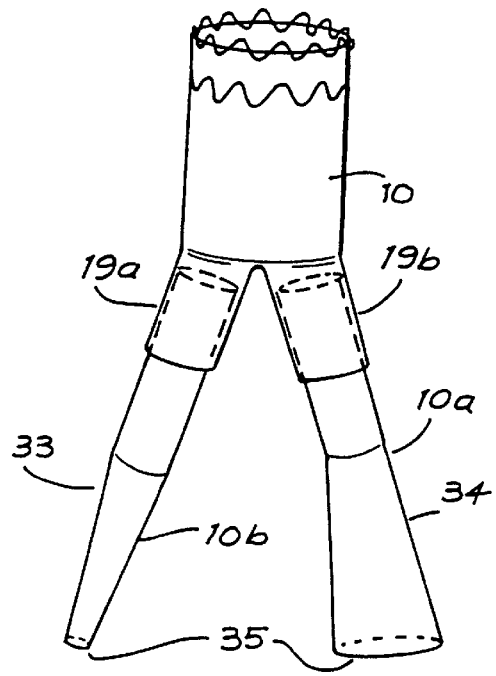
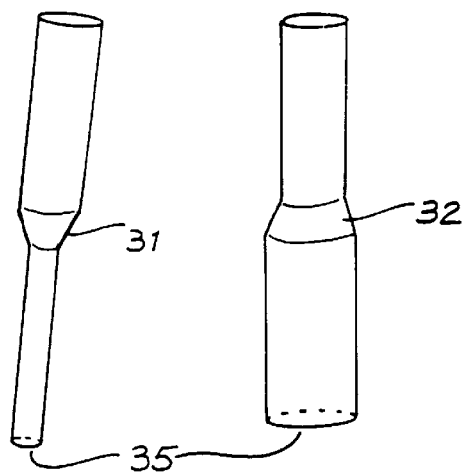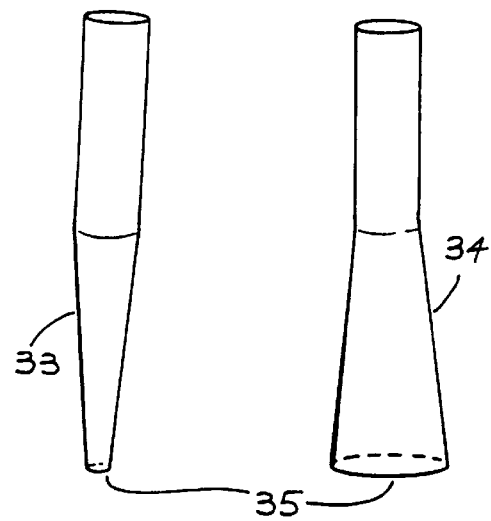
FIG. 8
a b c d e f

DELIVERY CATHETER AND METHOD FOR POSITIONING AN INTRALUMINAL GRAFT

FIELD OF THE INVENTION

The present invention relates to a method for positioning an intraluminal graft into a bifurcated artery and to a catheter for use in that method.

BACKGROUND ART

It is well known that through disease, arteries of humans are susceptible to the development of distended sacs known as aneurysms which are susceptible to rupture. Traditionally, aneurysms are treated by radical surgical intervention. This approach is risky for the patient and is, in many cases, not feasible due to other pre-existing disease states in the patient. More recently there have been a number of proposals for the intraluminal placement of an intraluminal graft bridging the aneurysms and thereby isolating an active arterial duct from the aneurysmal sac. One such arrangement is described in Australian Patent Application No. 78035/94.

Difficulties arise in the placement of such intraluminal grafts when the aneurysm extends from a single artery into one or more divergent arteries. In this case a so called "trouser graft" must be used. In such a graft a single tubular body bifurcates into two smaller tubular bodies. The intention being that the single tubular body is placed in the single artery and the two smaller tubular bodies are respectively placed in the two divergent arteries (for example, see U.S. Pat. No. 5,360,443 to Barone). In practice it has proven very difficult to effectively place a trouser graft.

The present invention relates to a new method and catheter designed to facilitate the placement of an intraluminal graft in a bifurcating artery.

DISCLOSURE OF THE INVENTION

In a first aspect the present invention comprises a delivery catheter comprising:

(a) an elongate catheter having a first end and a second end;

(b) an intraluminal graft having a body disposed about the elongate catheter, the body having at a first end, disposed adjacent to the first end of the elongate catheter, a tubular portion, and at a second end a bifurcation into first and second tubular graft extensions, the elongate catheter extending up the first tubular graft extension and into the tubular portion; and (c) a supplementary guidewire extending in a first direction through the first tubular graft extension and projecting in a second different direction into the second tubular graft extension.

In another aspect, the present invention consists of a method for positioning an intraluminal graft into a branching vessel within a patient's body, the vessel comprising a single pre-branching vessel branching into a pair of post-branching vessels, the method comprising:

(a) introducing into one of the post-branching vessels a first intraluminal graft having a body having at a first end a tubular portion and a second end that is bifurcated into first and second tubular graft extensions, there being positioned within the first intraluminal graft a guidewire which extends in a first direction through the first tubular graft extension and projects in a second different direction into the second tubular graft extension;

(b) positioning the first end of the first intraluminal graft and the second tubular graft extension within the pre-branching vessel and expanding that graft until at least the first end thereof expands into contact with a circumferential wall of the pre-branching vessel;

(c) extending the guidewire relative to the graft in the second different direction until it extends into the other of the post-branching vessels; and (d) introducing a second intraluminal graft, having an upstream end and downstream end, into the other of the post-branching vessels and, utilising the guidewire, or another guidewire positioned in its place, moving the second intraluminal graft until its upstream end is within or surrounds the second tubular graft extension and its downstream end is within the other of the post-branching vessels and causing the upstream end of the second intraluminal graft to form fluid conveying engagement with the second tubular graft extension.

The catheter and method according to this invention preferably utilise balloon expandable grafts made according to the disclosure of Australian Patent Application No. 78035/94, the contents thereof are incorporated herein by reference. The elongate catheter can have an inflatable balloon at or adjacent one end with the intraluminal graft disposed about the balloon. Other suitable balloon expandable or self-expandable stents or grafts could be used in carrying out the present invention.

In a preferred embodiment of the invention, the intraluminal grafts that are positioned at least partially in the post-branching vessels are provided in varying diameters. This ensures that a suitable graft is available to meet the varying diameters of post-branching vessels that are routinely operated upon in practice. In one embodiment, the variation in diameter of the intraluminal graft is achieved by a taper inwardly or outwardly of the outside diameter along at least a portion of the length of the shaft. Alternatively, the change in diameter is provided by a shorter step-down or step-up taper between two substantially cylindrical portions of different diameter which constitute the graft. Preferably, the upstream ends of the intraluminal grafts are of a standard diameter so as to provide a reliable connection with the respective tubular graft extensions of the intraluminal graft positioned wholly within the pre-branching vessel.

The present invention is hereafter described with reference to the placement of a trouser graft in a bifurcating artery, which is a typical application. The invention could, however, be used in other bodily vessels such as veins and bile ducts.

It is preferred that the intraluminal graft is of such a length that each of the tubular graft extensions terminates upstream of the bifurcation in the artery. In this arrangement a separate tubular graft is used to link each tubular extension with its associated distal artery. In an alternative arrangement the intraluminal graft includes one tubular extension long enough to project into the first of the distal arteries. In this case the other tubular extension terminates above the bifurcation and a second, tubular, graft joins that extension with the second distal artery.

The guidewire which extends upstream through the first tubular graft extension and downstream through the second is preferably very fine and substantially kink resistant. In one embodiment, the supplementary guidewire can extend through a channel in the graft body. In another embodiment, a supplementary catheter can extend upstream through the first tubular graft extension and downstream into the second of the tubular graft extensions, the supplementary catheter containing the guidewire. A supplementary catheter of 3 French is particularly preferred. The supplementary catheter and guidewire may be laid loosely into the graft before it is packaged about the elongate catheter. Alternatively, the supplementary catheter may be linked to the graft body for part of its length. In another alternative a part of the catheter may be interwoven with, or otherwise connected to, a part of the graft. In a further alternative, the supplementary catheter may be incorporated into a channel in the fabric of the graft wall. These various techniques are designed to better hold the supplementary guidewire and its associated catheter in place during insertion of the graft into the arterial system.

In a still further aspect, the present invention consists of a method for positioning an intraluminal graft across an aneurysm which extends from the aorta into both iliac arteries within a patient's body, the method comprising the steps of:

(a) making an incision or puncture to expose one of the patient's femoral arteries;

(b) inserting a first guidewire through the exposed femoral artery, the corresponding iliac artery and the aorta such that it traverses the aneurysm;

(c) guiding a first catheter sheath over the first guidewire until it traverses the aneurysm;

(d) withdrawing the first guidewire;

(e) inserting a second relatively stiff guidewire through the first catheter sheath until it traverses the aneurysm;

(f) withdrawing the first catheter sheath;

(g) guiding a second relatively larger diameter catheter sheath over the second guidewire until it traverses the aneurysm;

(h) guiding a first delivery catheter, which has a uninflated balloon adjacent one end with a first intraluminal graft disposed about the balloon, over the second guidewire and within the second larger diameter catheter sheath, the first intraluminal graft having a body having at a first end a tubular portion and a second end that is bifurcated into first and second tubular graft extensions, there being positioned within the first graft a third catheter containing a third guidewire which extends in a first direction through the first tubular graft extension and in a second different direction into the second tubular graft extension;

(i) positioning the first delivery catheter so that the first end of the first graft is upstream of the aneurysm;

(j) partially withdrawing the second larger diameter catheter sheath to free the first intraluminal graft;

(k) inflating the balloon and so expanding the first end of the first intraluminal graft until it engages against the wall of the aorta above the aneurysm;

(l) deflating the balloon to allow blood to flow down the first graft distending the first and second tubular graft extensions;

(m) guiding the third guidewire in the second direction downstream into the other of the iliac and femoral arteries;

(n) making an incision or puncture and retrieving the third guidewire from the other femoral artery;

(o) withdrawing the third catheter through the one femoral artery;

(p) guiding a fourth catheter sheath over the third guidewire and through the other femoral and iliac arteries until it is within the first graft and reaches at least to the top of the second tubular graft extension;

(q) withdrawing the third guidewire through the one femoral artery;

(r) guiding a fourth relatively large diameter guidewire through the fourth catheter sheath until the guidewire reaches at least the top of the second tubular graft extension;

(s) withdrawing the fourth catheter sheath through the other femoral artery;

(t) guiding a fifth relatively larger diameter catheter sheath over the fourth guidewire until the fifth catheter sheath reaches at least the top of the second tubular graft extension;

(u) guiding a second delivery catheter, which has a uninflated balloon adjacent one end with a second intraluminal graft, having an upstream end and a downstream end, disposed about the balloon, over the fourth guidewire and within the fifth larger diameter catheter sheath until the upstream end of the second graft is within the second tubular graft extension;

(v) partially withdrawing the fifth catheter sheath to free the second intraluminal graft;

(w) inflating the balloon on the second delivery catheter and so expanding the upstream end of the second intraluminal graft until it engages against the second tubular graft extension;

(x) maintaining the inflation of the balloon while withdrawing the first delivery catheter from the one femoral artery;

(y) once the first delivery catheter is removed from the one femoral artery deflating the balloon;

(z) fully withdrawing the fifth catheter sheath through the other femoral artery;

(aa) guiding a third delivery catheter, which has an uninflated balloon adjacent one end with a third intraluminal graft, having an upstream end and a downstream end, disposed about the balloon, over the second guidewire and within the second catheter sheath until the upstream end of the third graft is within the first tubular graft extension;

(bb) partially withdrawing the second catheter sheath to free the third intraluminal graft;

(cc) inflating the balloon on the third delivery catheter and so expanding the upstream end of the third intraluminal graft until it engages against the first tubular graft extension;

(dd) deflating the balloon on the third delivery catheter;

(ee) withdrawing the second delivery catheter through the other femoral artery and the third delivery catheter through the one femoral artery;

(ff) withdrawing the fourth guidewire and the fifth catheter sheath through the other femoral artery and suturing the incision or puncture in that artery;

(gg) withdrawing the second guidewire and second catheter sheath through the one femoral artery and suturing the incision or puncture in that artery.

BRIEF DESCRIPTION OF THE DRAWINGS

FIG. 2 is a side elevational view of one embodiment of a tubular intraluminal graft for use in the method according to the method described with reference to FIG. 1;

FIG. 3 is a longitudinal diametric sectional view through the intraluminal graft of FIG. 2;

FIG. 6b is an enlarged view of the inflatable balloons adjacent respectively the free end of a catheter and guidewire, with the balloons inflated;

FIG. 6c is a longitudinal sectional view of the device of FIG. 6b with the balloons uninflated;

FIGS. 7a to 7i show the stages of carrying out a method according to the present invention;

FIGS. 8a to 8f are simplified side elevational views of further alternative intraluminal grafts for use in the method according to the present invention.

PREFERRED MODE OF CARRYING OUT THE INVENTION

Figure 1:
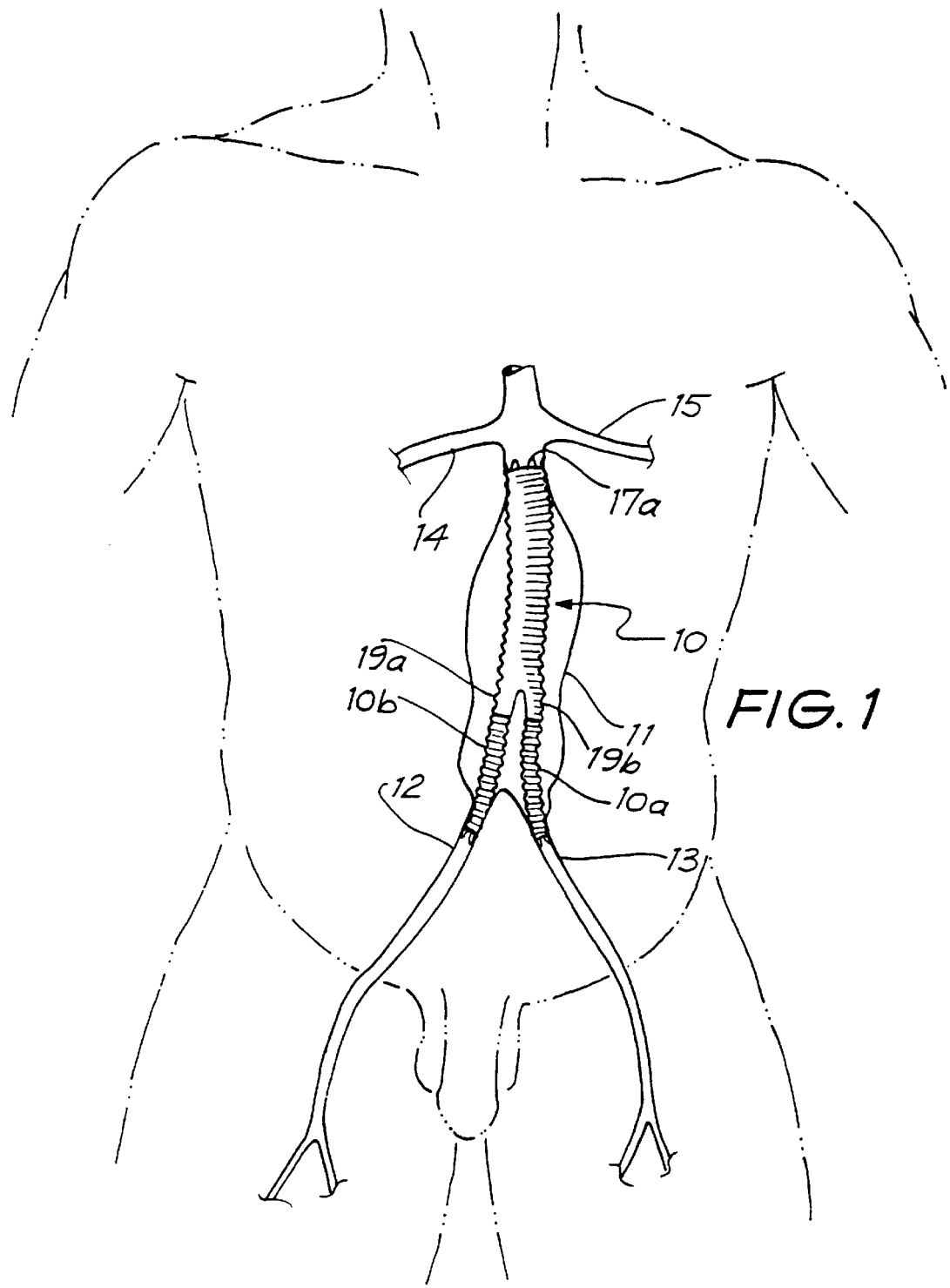
FIG. 1 is a diagrammatic partially cut-away central view of a patient with an aortic aneurysm which has been bridged by an intraluminal graft according to the present invention.
Figure 5:
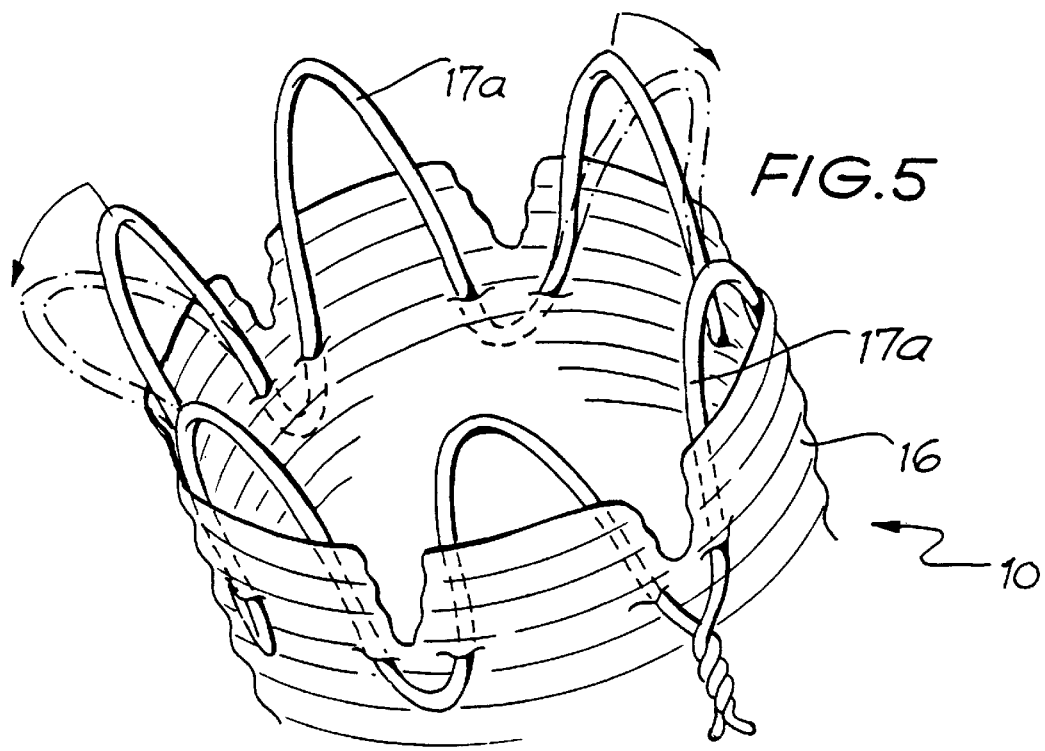
FIG. 5 is a detailed perspective view of the first end of the intraluminal graft of FIG. 4 showing how the alternate crests of the end wire of the graft are pushed radially outward during insertion of the graft.
Figure 4:
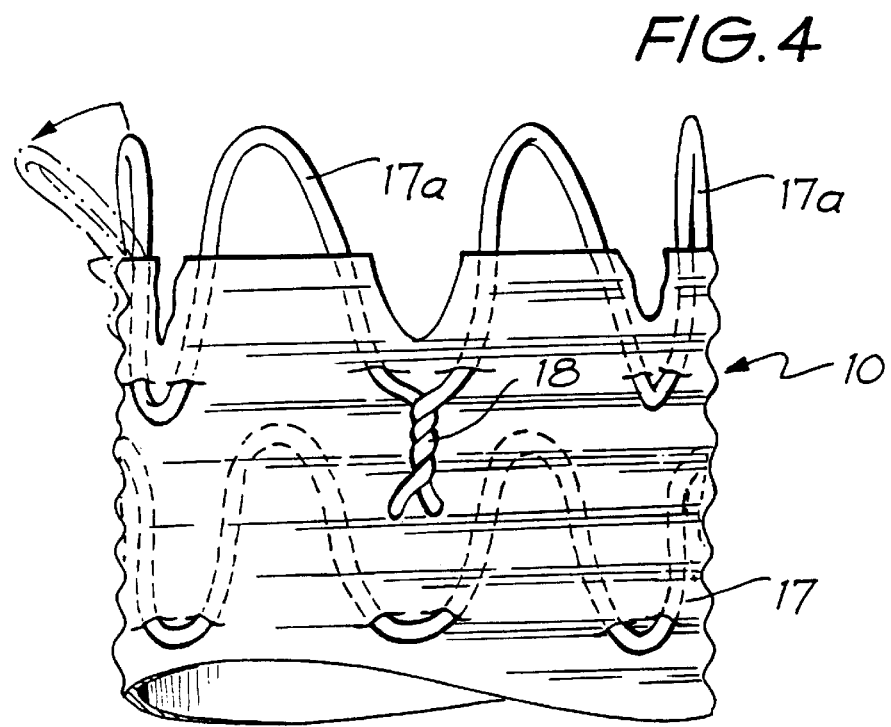
FIG. 4 is a detailed elevational view of one end of the intraluminal graft of FIG. 2.

A bifurcated or trouser graft comprising the three intraluminal grafts 10, 10a and 10b is adapted for insertion transfemorally into a patient to achieve bridging and occlusion of an aortic aneurysm extending into the left iliac artery. As is seen in FIG. 1 the aorta 11 is connected to the left and right iliac arteries 13 and 12. The aortic aneurysm is located between the renal arteries 14 and 15 and the iliac arteries 12 and 13 with the aneurysm extending down the left iliac artery 13.

Each intraluminal graft (as is shown in FIGS. 2–5) can comprise a crimped tube 16 of woven polyester. Other materials could be utilised including polytetrafluoroethylene, polyurethane and composites thereof. The tube 16 is reinforced along its length by a number of separate and spaced apart stainless-steel wires 17 (each of which can have the depicted generally closed sinusoidal shape). The wires 17 are preferably as thin as possible and are typically 0.3 to 0.4 mm in diameter. The wires 17 are malleable and may be bent into any desired shape, ie they are not resilient to any substantial extent so that they have to be physically expanded into contact with the aorta rather than expanding by virtue of their own resilience. The wires 17 are each woven into the fabric of the tube 16 such that alternate crests of each wire 17 are outside the tube 16 with the remainder of that wire 17 inside the tube 16 (except in the case of the endmost wires 17 as will be hereinafter described). The ends of each wire 17 are located outside the tube 16 and are twisted together to form a tail 18. While the ends are depicted as twisted together to form a tail 18, the ends can also be crimped together. The tails 18 of alternate wires 17 are bent to extend in opposite longitudinal directions along the outside surface of the tube 16.

The endmost wires 17a overhang the respective ends of the tube 16 so that alternate crests of those wires 17a extend longitudinally beyond the end of the tube 16. The endmost wires 17a preferably have an amplitude of about 6 mm and a wavelength such that between six and eight crests are spaced around the circumference of a 22 mm diameter graft. The next two adjacent wires 17 preferably are spaced as close as possible to the endmost wire 17a and respectively have amplitudes of 4 mm and 5 mm. These wires will typically have the same wavelength initially as the endmost wire 17a. Thereafter, throughout the graft the wires 17 are spaced at 15 mm intervals, have an amplitude of 6 mm, and have substantially the same initial wavelength as the endmost wire 17a.

As the aneurysm extends beyond the branching of the iliac arteries 12 and 13 from the aorta 11 a single tubular graft is insufficient to bridge the aneurysm while maintaining blood flow to each of the iliac arteries 12 and 13. Rather than using a single tubular graft, in the present method three separate tubular grafts 10, 10a and 10b are used. The downstream end of a first one of the grafts 10 is provided with a bifurcation to form a pair of short tubular graft extensions 19a, 19b of the graft 10. The short tubular graft extensions 19a, 19b may be passively expandable by blood flow or actively expandable by balloon expansion or by spring self-expansion.

As is best depicted in FIGS. 8(a)–(f), the graft portions 10a and 10b which are adapted to extend into the respective iliac arteries 12,13 each have an upstream end having a common diameter. The upstream ends interlock with the respective extensions 19a, 19b of the graft 10 adapted to be positioned within the aorta 11. Preferably, this interlocking is achieved by balloon-expansion or spring self-expansion of the upstream ends such that there is a frictional engagement between the respective upstream ends and the extensions 19a, 19b.

In addition to having a straight cylindrical tube, the diameter of the downstream end 35 of the graft portions 10a and 10b can be provided in varying diameters so as to suit the diameter of the iliac artery into which graft portions 10a and 10b are being implanted.

The change in diameter can be provided by a short step-down portion 31 (see FIG. 8c) or a step-up portion 32 (see FIG. 8d) or by a region of taper 33 and 34 extending along a length of the graft portion 10a or 10b (see FIGS. 8e and 8f).

The method for positioning the intraluminal graft will now be described with reference to FIGS. 7a–7i. In carrying out the method an incision or puncture is made to expose one of the femoral arteries (eg: ipsilateral), which flows from the corresponding iliac artery, and using the Seldinger needle technique, a 0.035" diameter floppy tipped flexible guidewire is inserted into and through the femoral artery and then the iliac artery 12 into the aorta 11 such that it traverses the aneurysm. An 8 French haemostatic sheath is then introduced over the wire to control bleeding. An angiographic catheter is introduced to allow an angiogram to be taken of the patient to show the position of the renal arteries 14, 15 and other relevant anatomical structures in the patient.

Figure 7B:
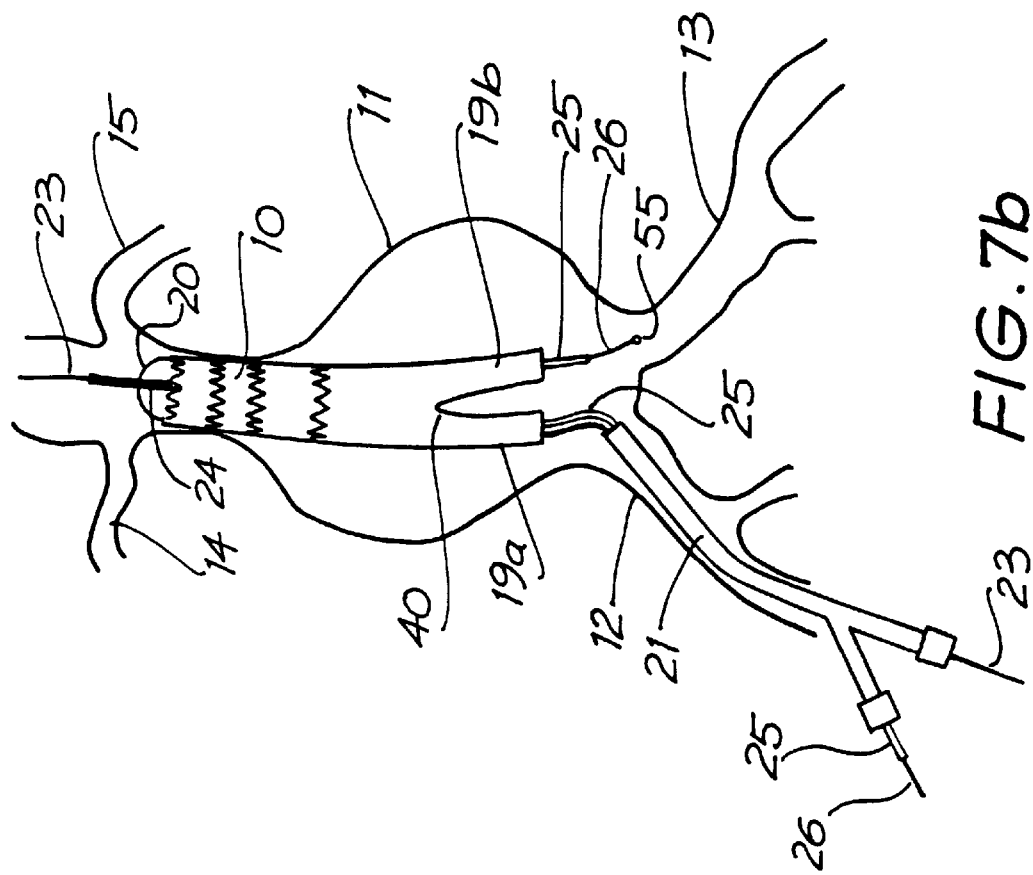
Figure 7A:
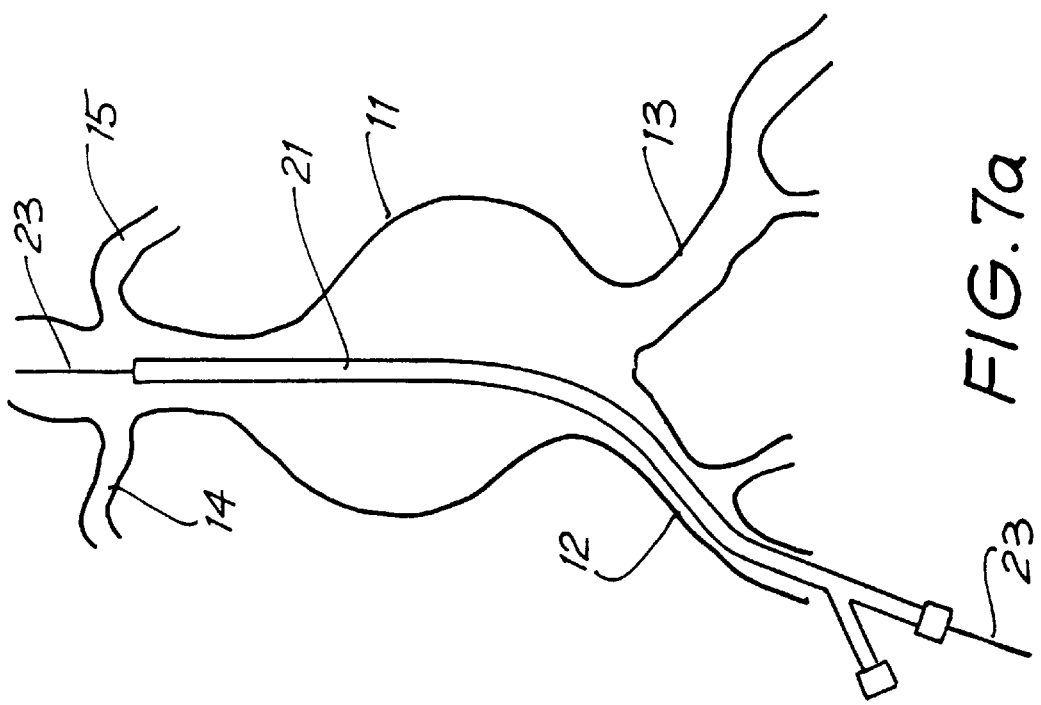
Figure 7D:
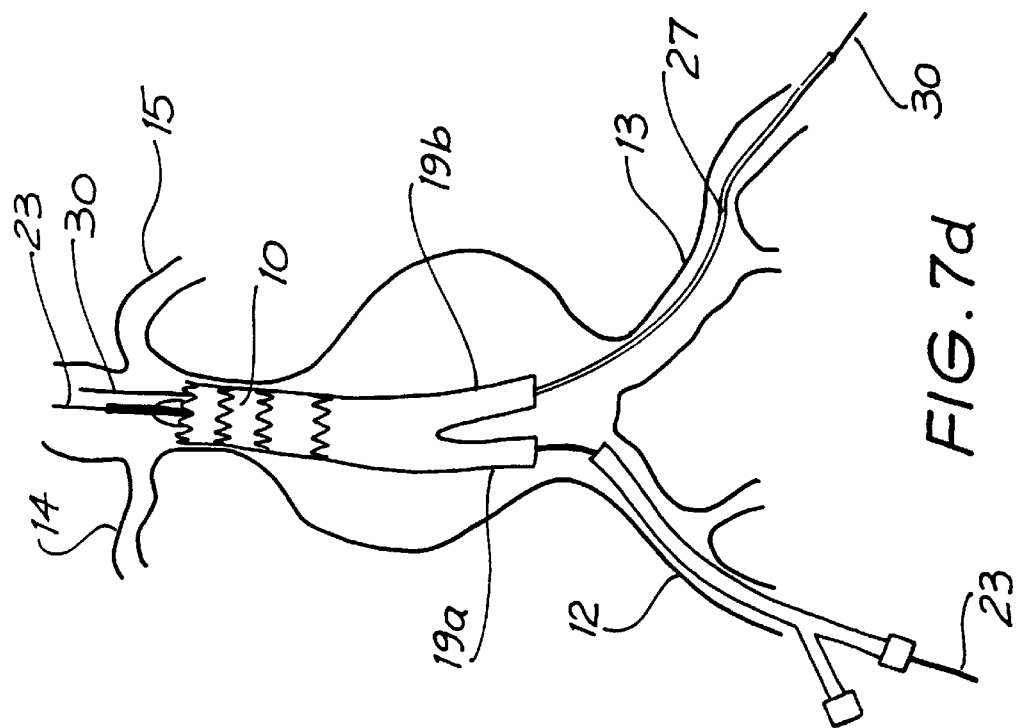

The floppy tipped flexible guidewire is then withdrawn and an Amplatz extra stiff (AES) guidewire 23 (0.035" diameter) is then passed through the angiographic catheter into the aorta 11 (see FIG. 7a). After withdrawal of the angiographic catheter, the stiff guidewire 23 is left in situ. A catheter sheath 21, preferably of 24 French, and trocar are then introduced into the aorta 11 over the stiff guidewire 23 (see FIG. 7a). A balloon catheter 24 is then introduced into the sheath 21.

Figure 6:
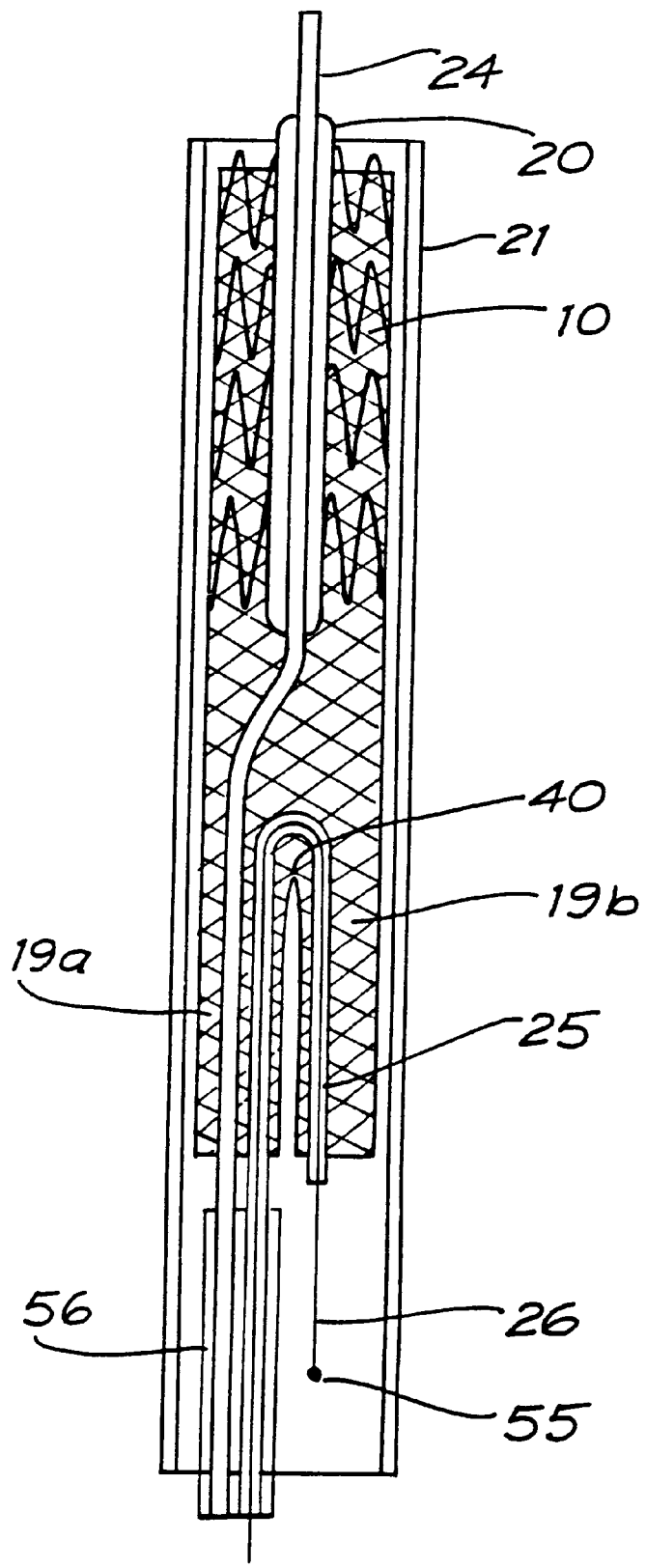
FIGS. 6 and 6a are vertical sectional views of two embodiments of possible bifurcated grafts mounted over delivery catheters for use in carrying out the present method.

As is depicted in more detail in FIG. 6, the balloon catheter 24 is a delivery catheter which is pre-packaged with a bifurcated graft 10, having the first and second tubular graft extensions 19a, 19b separated at a bifurcation point 40, and a thin catheter 25 containing a guidewire 26 extending in a first direction up through the first tubular extension 19a and then in a second different direction into the second graft extension 19b.

The catheter 24 and thin catheter 25 can be linked together below the graft 10 in a common catheter sheath 56 which serves to better ensure correct positioning of the catheter 25 and guidewire 26 on placement of the graft 10 in the vessel. In addition to being slidable through the tubular graft extensions 19a,19b, the catheter 25 can be fixed in place in the graft 10 prior to insertion of the graft 10 into a vessel. The catheter 26 can be sutured, glued or woven into the body of the graft 10.

Figure 6A:
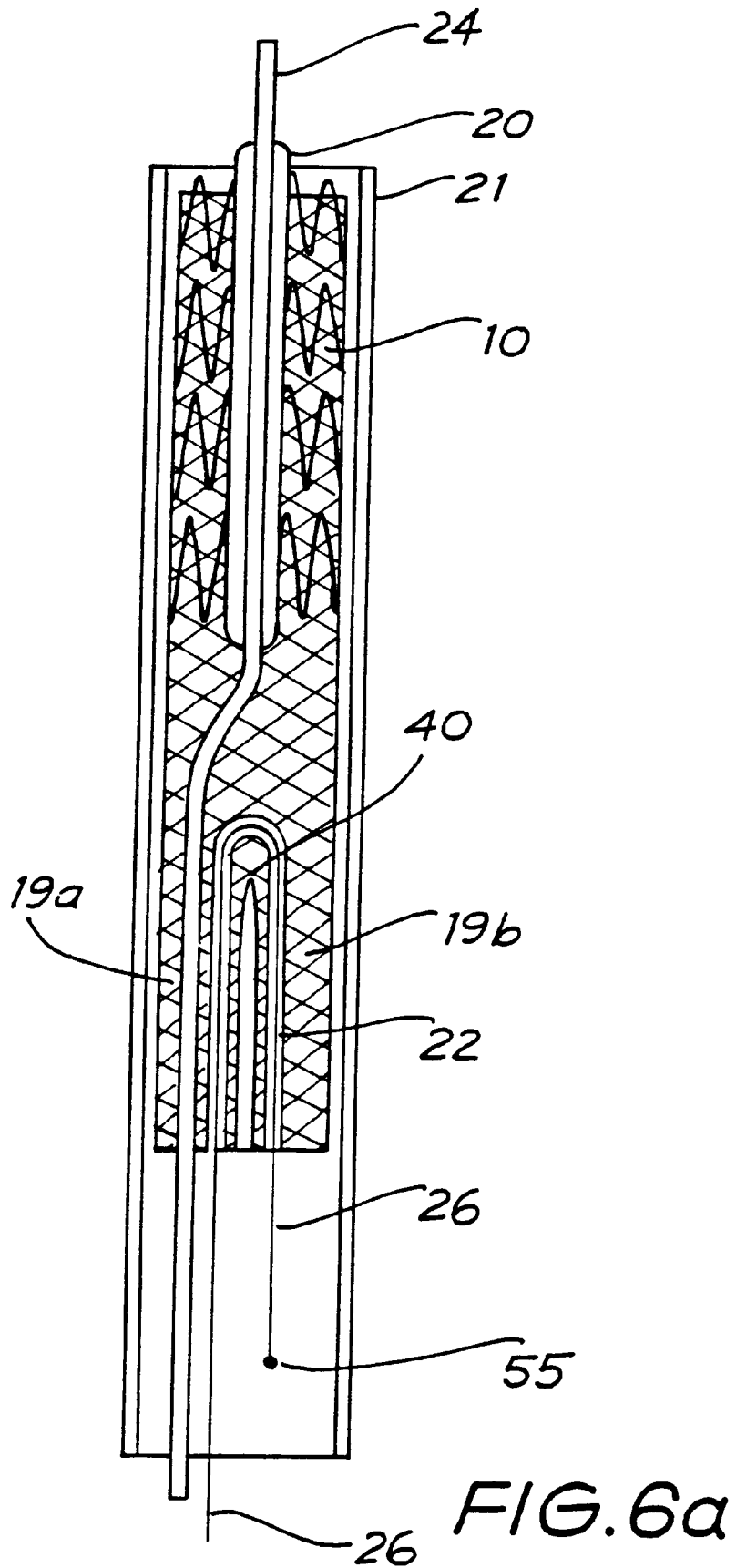

While the guidewire 26 is depicted in FIG. 6 inside a catheter 25, it can be readily envisaged that only the guidewire 26 could be disposed in the first and second tubular graft extensions 19a, 19b. In an alternative arrangement depicted in FIG. 6a, the guidewire 26 is positioned within a tubular channel 22 formed in the body of the graft 10. The channel 22 serves to ensure that the guidewire 26 remains in the desired position in the first and second tubular graft extensions 19a, 19b following packaging of the graft 10 about the balloon 20 and before placement of the balloon catheter 24 in the aorta 11.

When the balloon catheter 24 is positioned within the aorta 11 at the desired position, the sheath 21 is partially withdrawn to free the graft 10 and the balloon 20 inflated (see FIG. 7b). The inflation of the balloon 20 of catheter 24 expands the upstream end of the first graft 10 and causes it to engage its upstream end against the aorta wall above the aneurysm but downstream of the renal arteries 14 and 15. The first graft 10 is of such a length that the short tubular graft extensions 19a, 19b are disposed wholly within the aorta 11. The balloon 20 is then deflated but the balloon catheter 24 is left in place for the time being (see FIG. 7c). Deflation of the balloon 20 will allow blood to flow down the graft 10 distending each of the tubular graft extensions 19a, 19b.

Figure 7C:
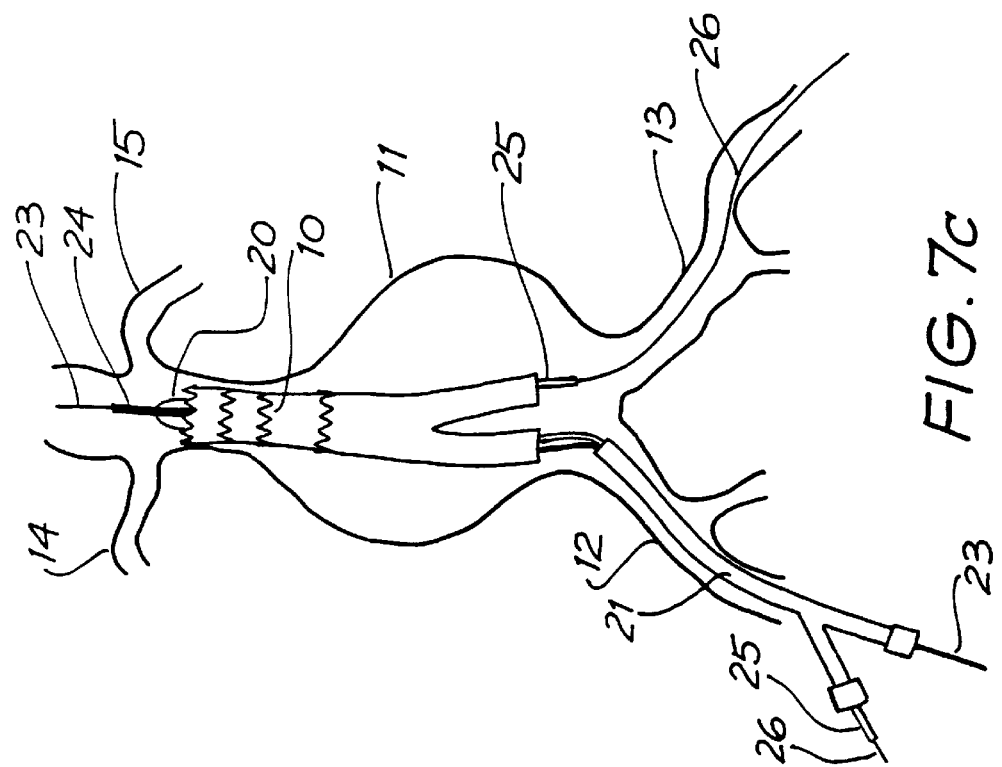
Figure 7F:
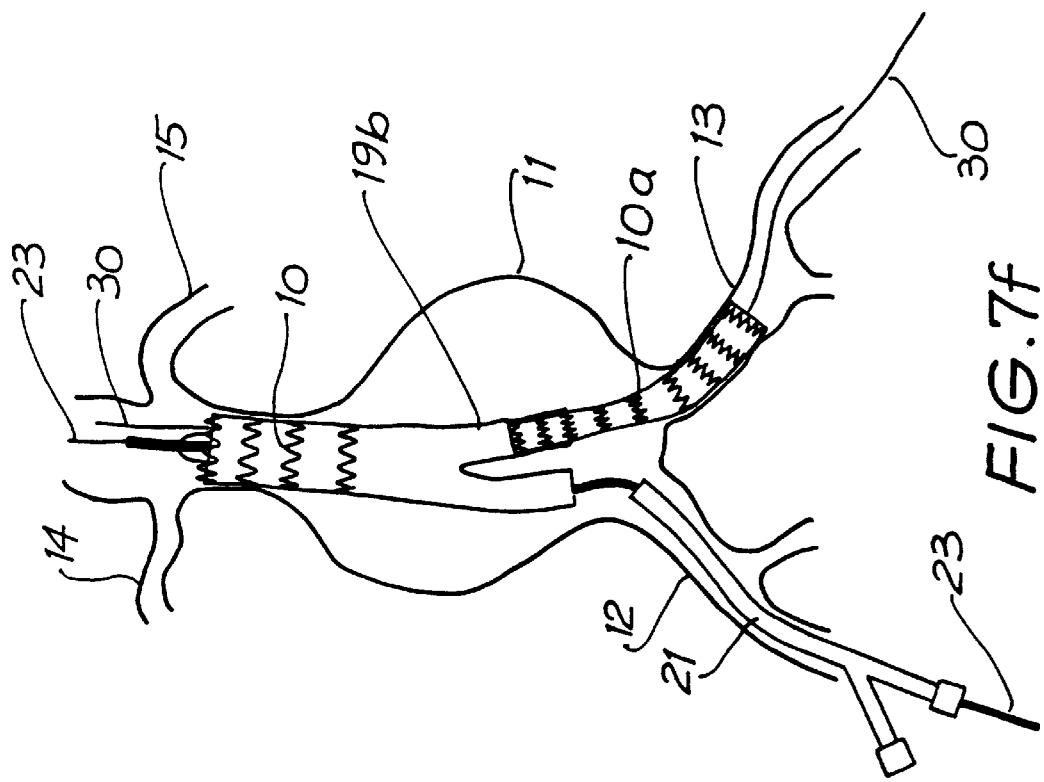
Figure 7E:
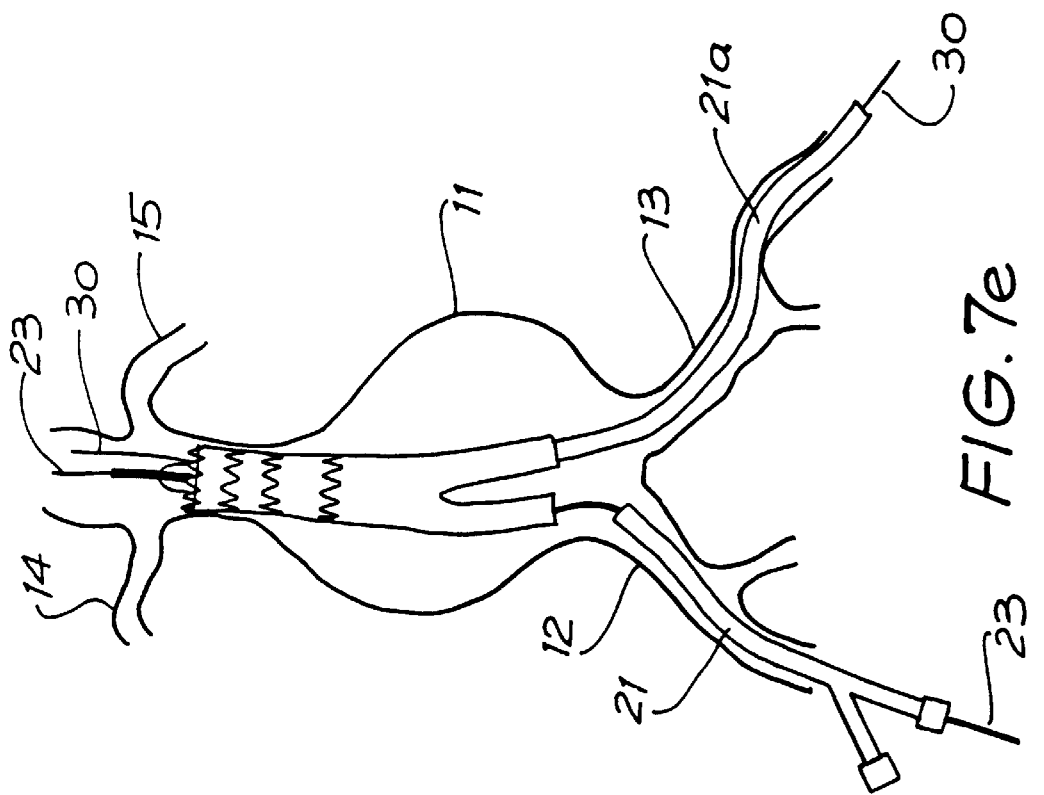

The thin catheter 25 is preferably 3 French and the guidewire 26 of a non-kinking material so that the guidewire 26 may be extended relative to the catheter 25 in a downstream direction (see FIG. 7c). The guidewire 26 may have at its tip a small inflatable balloon 55 or other flow impedance device as is depicted in FIG. 6. The balloon 55 can be inflated to help the guidewire 26 to be directed by blood flow into the contralateral iliac artery 13 as the guidewire 26 is extended. The guidewire 26 is preferably comprised of a Nitinol core having a hydrophilic coating. A balloon 50 can also be present on the free end of the catheter 25. The details of examples of such balloons 50,55 are depicted in more detail in FIGS. 6b and 6c. The balloons 50,55 are inflated to help respectively the catheter 25 and guidewire 26 to be carried and directed by blood flow into the contralateral iliac artery 13.

The enlarged view of the balloons 50,55 adjacent respectively the free ends of the catheter 25 and guidewire 26 provided by FIGS. 6b and 6c reveal the catheter 25 has two lumens 52 and 53. The guidewire 26 passes through the first lumen 52. The end of the second lumen 53 is sealed and a small hole 51 has been formed in the outer surface of the catheter 25. The latex balloon 50 is annularly bonded to the outer surface of the catheter 25 at 50a. When the balloon 50 is to be inflated, liquid or gas is injected down the second lumen 53 such that it passes through the hole 51 and inflates the balloon 50. Similarly, the guidewire 26 has a lumen 54 down which air can be injected to inflate the balloon 55 disposed at the free end of the guidewire 26.

Figure 6D:
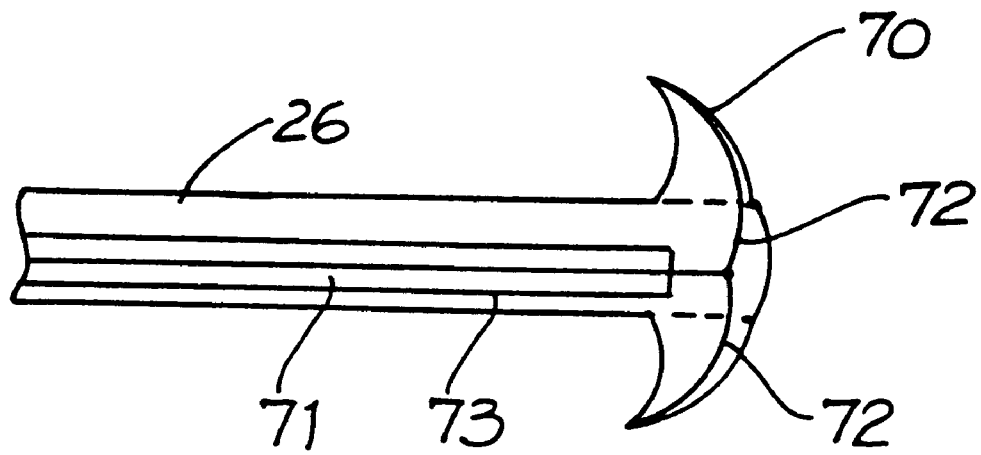
FIG. 6d is a simplified sectional view of a guidewire having an expandable umbrella adjacent its free end.
Figure 6E:
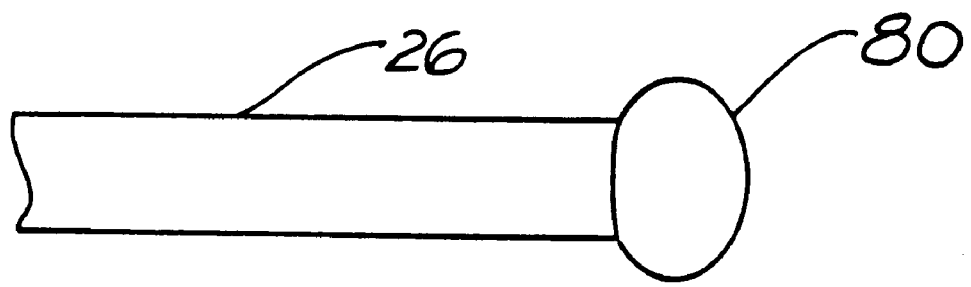
FIG. 6e is an alternative embodiment of FIG. 6d, wherein the guidewire has a small bead.

While inflatable balloons are preferred, other expandable devices can be envisaged. For example, in an alternative embodiment, the balloons 50,55 on the catheter 25 and guidewire 26 could be replaced by an expandable umbrella. An example of a type of umbrella that could be utilised is depicted in FIG. 6d. Disposed at the free end of the guidewire 26 is all umbrella 70. The umbrella 70, which is depicted in the expanded configuration in FIG. 6d, is expanded by a wire 71 extending through a lumen 72 in the guidewire 26. The wire 71 is attached to stays 72 so that on retraction of wire 71 the stays 72 articulate to expand the umbrella 70. While the umbrella 70 is on the guidewire 26 it can be readily envisaged that a similar arrangement could be utilised on the catheter 25. In a further alternative, the balloon 55 on the guidewire 26 can be replaced by a small solid bead 80 of material such as epoxy resin or titanium as depicted in FIG. 6e. The bead 80 preferably has a larger profile than the guidewire 26.

In certain applications it is desirable once the catheter 25 is in a desired position in a vessel to further expand the balloon 50 at the free end of the catheter 25 until the balloon 50 engages the wall of the vessel and holds the catheter 25 in a desired position within the vessel to provide additional anchorage during passage of the guidewire 26 through the vessel.

Once the guidewire 26 is correctly placed in the contralateral femoral artery, a cut down is effected to that femoral artery which is cross-clamped and an arteriotomy effected. If the guidewire 26 has been guided fully into the contralateral femoral artery, the guidewire 26 is simply recovered by drawing the guidewire through the incision or puncture in the artery. If the guidewire 26 has not been guided fully into the contralateral femoral artery, a snare or similar device can be introduced through the contralateral femoral artery to grab the guidewire 26 and draw it back to the incision or puncture site for retrieval. Once the guidewire 26 is retrieved, the thin catheter 25 is then withdrawn via the ipsilateral side and another catheter 27 is fed through the contralateral femoral artery up the guidewire 26 until it is within the first graft 10 and reaches at least to the top of the second tubular extension 19b (see FIG. 7d). The thin guidewire 26 is then withdrawn and a thicker guidewire 30 inserted through the contralateral femoral artery into the catheter 27. The catheter 27 is then removed and a catheter sheath 21a, preferably of 24 French, and trocar are introduced over the stiff guidewire 30 (see FIG. 7e).

Prior to extending the guidewire 26 into the contralateral iliac and femoral arteries, a catheter sheath (that can be similar to catheter sheath 21) can be extended upstream through the contralateral femoral and iliac arteries to reduce any tortuosity that may be present in these arteries and so facilitate guiding of the guidewire 26 therethrough.

Figure 9:
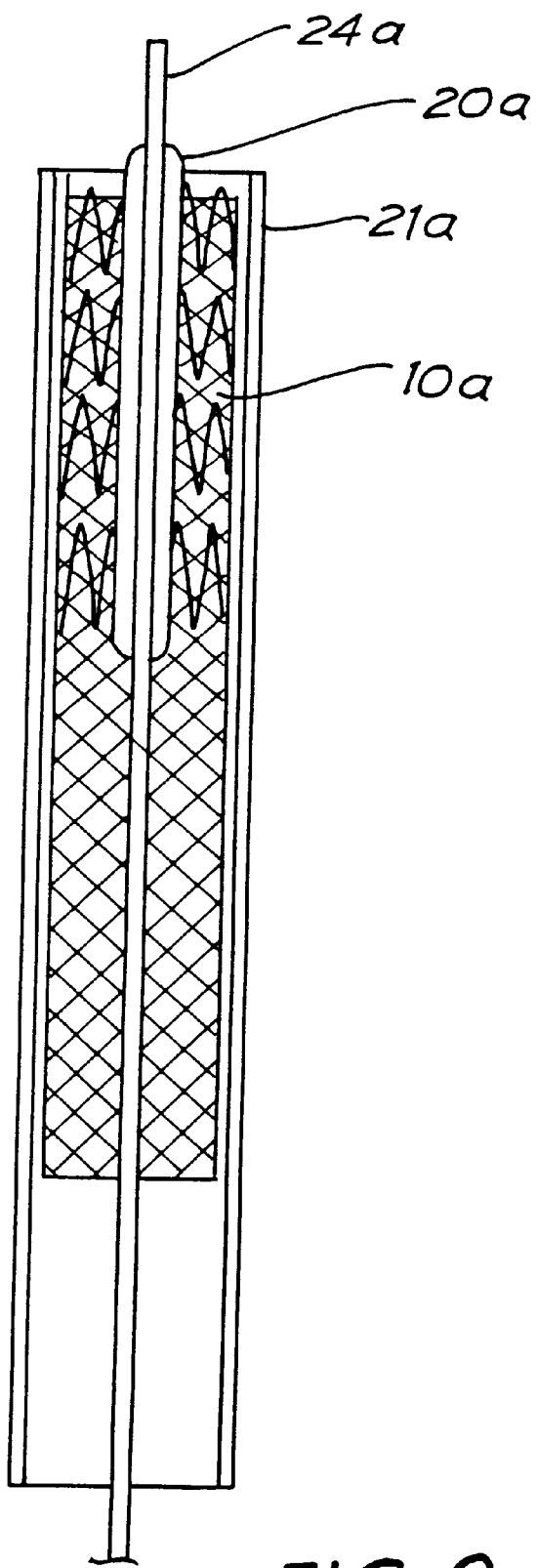
FIG. 9 is a vertical sectional view of one embodiment of a tubular graft mounted over a delivery catheter that can be used in carrying out the present method.

A second balloon catheter 24a, such as is depicted in FIG. 9, on which is packaged a second tubular graft 10a, is then introduced through catheter sheath 21a until its upper end is well within the second tubular extension 19b and within the iliac artery 13 at its lower end. The balloon 20a on the catheter 24a is inflated such that the upper end of graft 10a is frictionally engaged with the second tubular extension 19b (see FIG. 7f). The inflation of the balloon 20a on the catheter 24a supports the graft 10a during the withdrawal of the first balloon catheter 24 through the ipsilateral artery 12. Then the balloon 20a on the catheter 24a is deflated and the catheter 24a maintained in place to provide continued support for the grafts 10, 10a in the aorta 11 while the third graft 10b is positioned.

The catheter sheath 21a is then removed (see FIGS. 7f and 7g) and a third balloon catheter on which is packaged a tubular graft 10b (the third balloon catheter and graft 10b can be identical to that depicted in FIG. 9) is introduced into the sheath 21 on guidewire 23. It is advanced until its upstream end is within the first tubular extension 19a and, following partial withdrawal of the sheath 21, is then deployed. The third graft 10b positioned on the third balloon catheter is thus urged at its upstream end into contact with first tubular extension 19a and at its downstream end into contact with the right iliac artery 12 (see FIG. 7h).

Figure 7I:
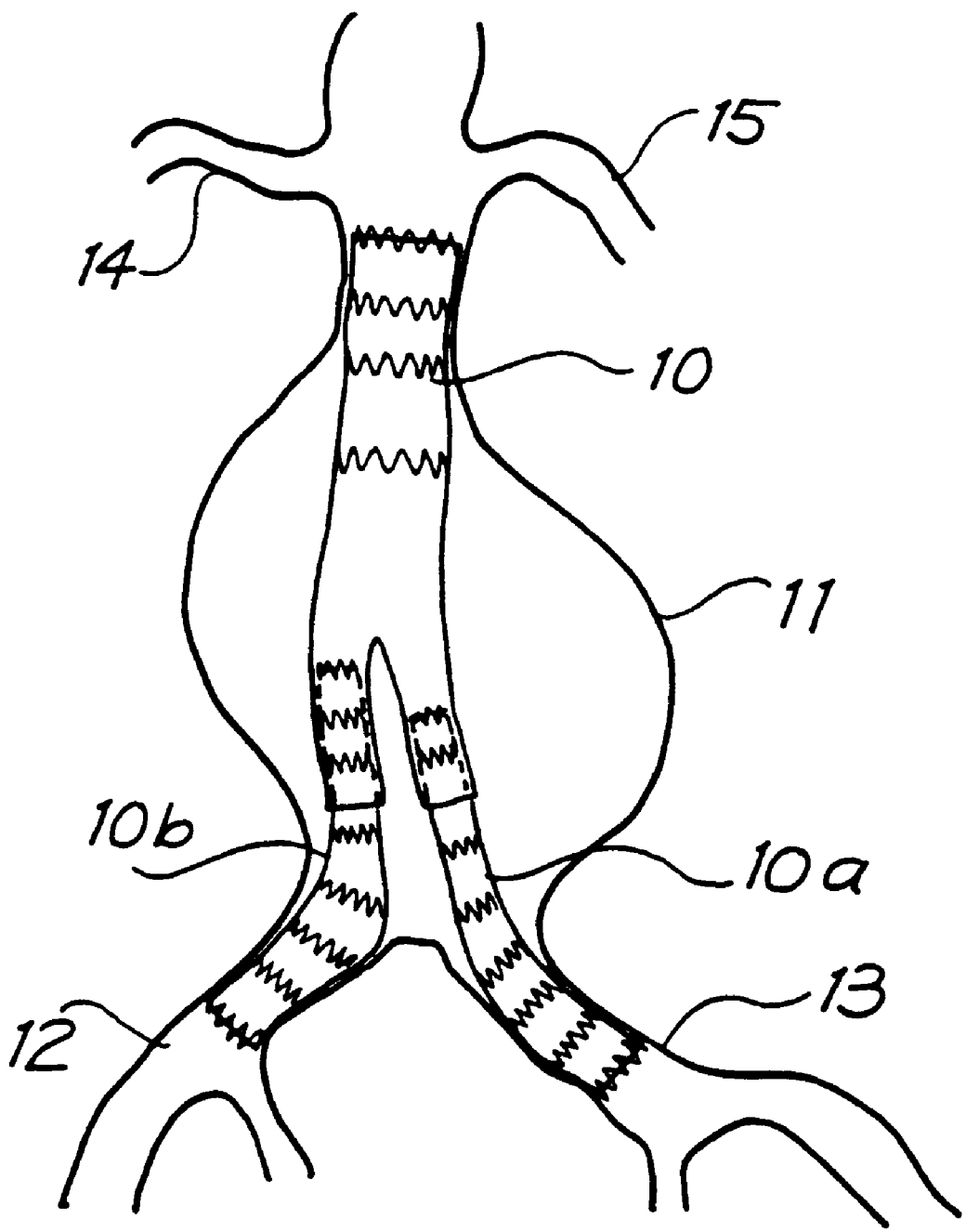

The stiff guidewires 23 and 30 are now withdrawn and the contralateral incision or puncture sutured. A second angiographic examination now takes place and if the grafts 10, 10a and 10b are correctly placed and functioning, the haemostatic sheath 21 is withdrawn and the right femoral incision or puncture sutured. The result is a functioning trouser graft bridging an aneurysm such as is depicted in FIG. 7i.

The operation may be carried out using a general anaesthetic, an epidural anaesthetic or, in suitable cases, using only a local anaesthetic.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

We claim:

1. A delivery catheter comprising:
   (a) an elongate catheter having a first end and a second end;
   (b) an intraluminal graft having a body disposed about the elongate catheter, the body having at a first end, disposed adjacent to the first end of the elongate catheter, a tubular portion, and at a second end a bifurcation into first and second tubular graft extensions, the elongate catheter extending up the first tubular graft extension and into the tubular portion; and
   (c) a supplementary guidewire extending in a first direction through the first tubular graft extension and projecting in a second different direction into the second tubular graft extension.

2. The delivery catheter of claim 1 wherein the supplementary guidewire extends through a channel in the graft body.

3. The delivery catheter of claim 1 wherein the elongate catheter has an inflatable balloon adjacent the first end and the intraluminal graft is disposed about the balloon.

4. The delivery catheter of claim 1 wherein a portion of the intraluminal graft proximate the first end is self-expandable.

5. The delivery catheter of claim 1 wherein one of the tubular graft extensions is of a greater length than the other tubular graft extension.

6. The delivery catheter of claim 1 wherein the guidewire is relatively thin and kink resistant.

7. The delivery catheter of claim 1 wherein the elongate catheter extends up the first tubular graft extension and through the tubular portion of the graft body.

8. The delivery catheter of claim 1 wherein the graft body is circumferentially supported along its length by a plurality of separate, spaced-apart wires each having a closed substantially sinusoidal continuously curved configuration having alternate apices.

9. The delivery catheter of claim 1 wherein the graft body is circumferentially supported along its length by a plurality of separate, spaced-apart wires, wherein each of the wires is interwoven with the graft body such that alternate portions of the wire are outside of the graft body with the remaining portions of the wire inside the graft body.

10. The delivery catheter of claim 1 wherein a supplementary catheter extends in the first direction through the first tubular graft extension and in the second direction into the second tubular graft extension, the supplementary catheter containing the supplementary guidewire.

11. The delivery catheter of claim 10 wherein the supplementary catheter is a 3 French catheter.

12. The delivery catheter of claim 10 wherein the supplementary catheter extends in the first direction through the first tubular graft extension and in the second direction into and through the second tubular graft extension.

13. The delivery catheter of claim 10 wherein the supplementary catheter is linked for part of its length to the elongated catheter.

14. The delivery catheter of claim 10 wherein the guidewire projects from a free end of the supplementary catheter.

15. The delivery catheter of claim 10 wherein at least a portion of the supplementary catheter is connected to at least a portion of the intraluminal graft.

16. The delivery catheter of claim 15 wherein the supplementary catheter is incorporated into a channel in the body of the graft.

17. The delivery catheter of claim 1 wherein both the first and second tubular graft extensions are adapted to engage with a further tubular intraluminal graft.

18. The delivery catheter of claim 17 wherein the further tubular intraluminal graft varies in outside diameter along its length.

19. The delivery catheter of claim 18 wherein the variation in outside diameter is provided by an inward taper of the graft along a portion of its length.

20. The delivery catheter of claim 18 wherein the variation in outside diameter is provided by an outward taper of the graft along a portion of its length.

21. The delivery catheter of claim 18 wherein a first portion of the further tubular intraluminal graft has a first outside diameter and a second portion has a different outside diameter.

22. The delivery catheter of claim 1 wherein the graft body is circumferentially reinforced proximate its first end by a plurality of separate, spaced-apart malleable wires, each of which has a generally closed sinusoidal shape, a first wire being located adjacent to the first end such that alternate crests or apices of the first wire projects beyond at least part of the first end.

23. The delivery catheter of claim 22 within the first wire has a greater amplitude than the next adjacent wire, and preferably the next two adjacent wires.

24. The delivery catheter of claim 22 wherein wires adjacent the first end of the graft are more closely spaced than wires distal the first end.

25. The delivery catheter of claim 22 wherein the graft body is fabricated from polyester, polytetrafluoroethylene, polyurethane or a composite thereof.

26. The delivery catheter of claim 22 the wires are interwoven with the graft body.

27. The delivery catheter of claim 26 the ends of each wire are twisted together on the outside of the graft body.

28. The delivery catheter of claim 1 wherein the tubular graft body is circumferentially supported along its length by a plurality of separate, spaced-apart wires, with a first wire being located adjacent the first end of the graft body such that portions of the first wire project beyond at least part of the first end.

29. The delivery catheter of claim 28 wherein each of the wires is interwoven with the graft body such that alternate portions of each wire are outside of the graft body with the remaining portions of each wire inside the graft body.

30. The delivery catheter of claim 28 wherein the graft body comprises a plurality of holes and wherein each of the wires are threaded through the holes such that alternate portions of the wire are outside of the graft body with the remaining portions of the wire inside the graft body.

31. The delivery catheter of claim 28 wherein the wires are sutured to the graft body.

32. The delivery catheter of claim 28 in which each end of the graft body is provided with a wire which has alternate crests or apices extending beyond the adjacent end of the graft body.

33. The delivery catheter of claim 32 wherein the wires adjacent the first end of the graft body are more closely spaced apart from each other than the wires intermediate the two ends of the graft body.

34. The delivery catheter of claim 33 wherein the first wire has a greater amplitude and a smaller wavelength than a majority of the other wires in the graft body.

35. The delivery catheter of claim 28 wherein each wire has a closed substantially sinusoidal continuously curved configuration having alternate apices, and wherein alternate apices of the first wire project beyond at least part of the first end.

36. The delivery catheter of claim 35 wherein the wavelength of the wires is substantially constant along the length of the graft body.

37. The delivery catheter of claim 35 wherein the first wire has a greater amplitude than the wire adjacent to it.

38. The delivery catheter of claim 35 wherein the first end of the graft body comprises an edge, and wherein the edge of the first end is scalloped between each projecting apex of the first wire.

39. The delivery catheter of claim 28 wherein each wire comprises two opposing ends, and wherein both ends of each wire are joined together on the outside of the graft body.

40. The delivery catheter of claim 39 wherein the joined ends of adjacent wires project in opposite directions along the graft body.

41. The delivery catheter of claim 39 wherein both ends of each wire are twisted or crimped together.

42. A method for positioning an intraluminal graft into a branching vessel within a patient's body, the vessel comprising a single pre-branching vessel branching into a pair of post-branching vessels, the method comprising:
(a) introducing into one of the post-branching vessels a first intraluminal graft having a body having at a first end a tubular portion and a second end that is bifurcated into first and second tubular graft extensions, the body being disposed about a first elongate catheter, and there being positioned within the first intraluminal graft a supplementary guidewire which extends in a first direction through the first tubular graft extension and projects in a second different direction into the second tubular graft extension;
(b) positioning the first end of the first intraluminal graft and the second tubular graft extension within the pre-branching vessel and expanding that graft until at least the first end thereof expands into contact with a circumferential wall of the pre-branching vessel;
(c) extending the supplementary guidewire relative to the graft in the second different direction until it extends into the other of the post-branching vessels; and
(d) introducing a second intraluminal graft, having an upstream end and downstream end, into the other of the post-branching vessels and, utilising the supplementary guidewire, or another guidewire positioned in its place, moving the second intraluminal graft until its upstream end is within or surrounds the second tubular graft extension and its downstream end is within the other of the post-branching vessels and causing the upstream end of the second intraluminal graft to form fluid conveying engagement with the second tubular graft extension.

43. The method of claim 42 wherein the steps of introducing the second intraluminal graft into the other of the post-branching vessels and moving it until its upstream end is within the second tubular graft extension comprise:
(a) guiding a second elongate catheter, which has an uninflated balloon adjacent one end with the upstream end of the second intraluminal graft disposed about the balloon, over a smaller diameter guidewire and within a larger diameter catheter sheath pre-positioned in the other post-branching vessel and the pre-branching vessel;
(b) partially withdrawing the catheter sheath to free the second intraluminal graft;
(c) inflating the balloon and so expanding the upstream end of the second intraluminal graft until it engages against the second tubular graft extension;
(d) maintaining the inflation of the balloon while withdrawing the first elongate catheter from the one post-branching vessel; and
(e) once the first delivery catheter is removed from the one post-branching vessel deflating the balloon.

44. The method of claim 42 wherein the steps of introducing the first intraluminal graft into one of the post-branching vessels and positioning the first end and the second tubular graft extension within the pre-branching vessel comprise:
(a) guiding the first elongate catheter, which has a uninflated balloon adjacent one end with the first end of the first intraluminal graft disposed about the balloon, over a smaller diameter guidewire and within a larger diameter catheter sheath pre-positioned in the one post-branching vessel and pre-branching vessel;
(b) partially withdrawing the catheter sheath to free the first intraluminal graft;
(c) inflating the balloon and so expanding the first end of the first intraluminal graft until it engages against the pre-branching vessel wall; and
(d) deflating the balloon.

45. The method of claim 42 further comprising the step of:
(e) introducing a third intraluminal graft having an upstream end and a downstream end into the one post-branching vessel and moving the third intraluminal graft until its upstream end is within or surrounds the first tubular graft extension and its downstream end is within the one post-branching vessel and causing the upstream end of the third intraluminal graft to form fluid conveying engagement with the first tubular graft extension.

46. The method of claim 45 wherein the step of introducing the third intraluminal graft into the one post-branching vessel and moving it until its upstream end is within the first tubular graft extension comprises:
(a) guiding a third elongate catheter, which has an uninflated balloon adjacent one end with the upstream end of the third intraluminal graft disposed about the balloon, over a smaller diameter guidewire and within a larger diameter catheter sheath pre-positioned in the one post-branching vessel and the pre-branching vessel;

(b) partially withdrawing the catheter sheath to free the third intraluminal graft;

(c) inflating the balloon and so expanding the upstream end of the third intraluminal graft until it engages against the first tubular graft extension; and (d) deflating the balloon.

47. A method for positioning an intraluminal graft across an aneurysm which extends from the aorta into at least one iliac artery within a patient's body, the method comprising the steps of:

(a) making an incision or puncture to expose one of the patient's femoral arteries;

(b) inserting a first guidewire through the exposed femoral artery, the corresponding iliac artery and the aorta such that it traverses the aneurysm;

(c) guiding a first catheter sheath over the first guidewire until it traverses the aneurysm;

(d) withdrawing the first guidewire;

(e) inserting a second relatively stiff guidewire through the first catheter sheath until it traverses the aneurysm;

(f) withdrawing the first catheter sheath;

(g) guiding a second relatively larger diameter catheter sheath over the second guidewire until it traverses the aneurysm;

(h) guiding a first elongate catheter, which has a uninflated balloon adjacent one end with a first intraluminal graft disposed about the balloon, over the second guidewire and within the second larger diameter catheter sheath, the first intraluminal graft having a body having at a first end a tubular portion and a second end that is bifurcated into first and second tubular graft extensions, there being positioned within the first graft a third catheter containing a third guidewire which extends in a first direction through the first tubular graft extension and in a second different direction into the second tubular graft extension;

(i) positioning the first elongate catheter so that the first end of the first graft is upstream of the aneurysm;

(j) partially withdrawing the second larger diameter catheter sheath to free the first intraluminal graft;

(k) inflating the balloon and so expanding the first end of the first intraluminal graft until it engages against the wall of the aorta above the aneurysm;

(l) deflating the balloon to allow blood to flow down the first graft distending the first and second tubular graft extensions;

(m) guiding the third guidewire in the second direction downstream into the other of the iliac and femoral arteries;

(n) making an incision or puncture and retrieving the third guidewire from the other femoral artery;

(o) withdrawing the third catheter through the one femoral artery;

(p) guiding a fourth catheter sheath over the third guidewire and through the other femoral and iliac arteries until it is within the first graft and reaches at least to the top of the second tubular graft extension;

(q) withdrawing the third guidewire through the one femoral artery;

(r) guiding a fourth relatively large diameter guidewire through the fourth catheter sheath until the guidewire reaches at least the top of the second tubular graft extension;

(s) withdrawing the fourth catheter sheath through the other femoral artery;

(t) guiding a fifth relatively larger diameter catheter sheath over the fourth guidewire until the fifth catheter sheath reaches at least the top of the second tubular graft extension;

(u) guiding a second elongate catheter, which has a uninflated balloon adjacent one end with a second intraluminal graft, having an upstream end and a downstream end, disposed about the balloon, over the fourth guidewire and within the fifth larger diameter catheter sheath until the upstream end of the second graft is within the second tubular graft extension;

(v) partially withdrawing the fifth catheter sheath to free the second intraluminal graft;

(w) inflating the balloon on the second delivery catheter and so expanding the upstream end of the second intraluminal graft until it engages against the second tubular graft extension;

(x) maintaining the inflation of the balloon while withdrawing the first elongate catheter from the one femoral artery;

(y) once the first elongate catheter is removed from the one femoral artery deflating the balloon;

(z) fully withdrawing the fifth catheter sheath through the other femoral artery;

(aa) guiding a third elongate catheter, which has an uninflated balloon adjacent one end with a third intraluminal graft, having an upstream end and a downstream end, disposed about the balloon, over the second guidewire and within the second catheter sheath until the upstream end of the third graft is within the first tubular graft extension;

(bb) partially withdrawing the second catheter sheath to free the third intraluminal graft;

(cc) inflating the balloon on the third elongate catheter and so expanding the upstream end of the third intraluminal graft until it engages against the first tubular graft extension;

(dd) deflating the balloon on the third elongate catheter;

(ee) withdrawing the second elongate catheter through the other femoral artery and the third elongate catheter through the one femoral artery;

(ff) withdrawing the fourth guidewire and the fifth catheter sheath through the other femoral artery and suturing the incision or puncture in that artery;

(gg) withdrawing the second guidewire and second catheter sheath through the one femoral artery and suturing the incision or puncture in that artery.

48. The method of claim 47 wherein in an alternative step (l) the first and second tubular graft extensions are distended respectively by an inflatable balloon or are self-expandable.

* * * * *